United States Patent [19]

Barnes et al.

[11] 4,242,267
[45] Dec. 30, 1980

[54] PROCESS FOR PREPARING 5-ALKYL-7-(S-ALKYL-SULFONIMIDOYL)-XANTHONE-2-CARBOXYLIC ACIDS

[75] Inventors: Alan C. Barnes, Cirencester; Peter D. Kennewell, Swindon, both of England

[73] Assignee: Roussel Uclaf, Paris, France

[21] Appl. No.: 118,523

[22] Filed: Feb. 4, 1980

[51] Int. Cl.³ .......................................... C07D 311/86
[52] U.S. Cl. ..................................... 260/335; 564/91
[58] Field of Search .................................. 260/335

[56] References Cited

U.S. PATENT DOCUMENTS

| | | | |
|---|---|---|---|
| 3,849,565 | 11/1974 | Pfister et al. | 260/335 |
| 4,024,276 | 5/1977 | Barnes et al. | 260/335 |
| 4,078,078 | 3/1978 | Barnes et al. | 260/335 |

FOREIGN PATENT DOCUMENTS

| | | |
|---|---|---|
| 2145654 | 2/1973 | France . |
| 2167487 | 8/1973 | France . |
| 2167490 | 8/1973 | France . |
| 2277576 | 2/1976 | France . |
| 2423487 | 11/1979 | France . |

*Primary Examiner*—Norma S. Milestone
*Attorney, Agent, or Firm*—Hammond & Littell, Weissenberger and Muserlian

[57] ABSTRACT

A novel process for the preparation of xanthane-2-carboxylic acids of the formula

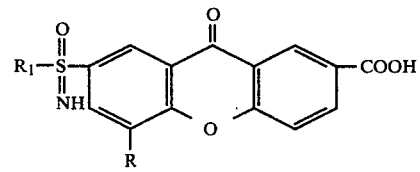

wherein R is selected from the group consisting of hydrogen and alkyl of 1 to 9 carbon atoms and $R_1$ is alkyl of 1 to 5 carbon atoms which possess an antiallergic activity and are particularly useful for treating asthma and asthmatic form bronchitisis of allergic origin.

5 Claims, No Drawings

PROCESS FOR PREPARING 5-ALKYL-7-(S-ALKYL-SULFONIMIDOYL)-XANTHONE-2-CARBOXYLIC ACIDS

STATE OF THE ART

The compounds of formula I and their preparation are described in French Pat. No. 2,277,576 which also describes their utility. Another process for the preparation of the said compounds is described in published French patent application No. 2,423,487. Other pertinent prior art are U.S. Pat. Nos. 3,849,565, 4,024,276 and 4,078,078 and French Pat. Nos. 2,145,654, 2,167,487 and 2,167.490.

OBJECTS OF THE INVENTION

It is an object of the invention to provide an improved process for the preparation of the compounds of formula I.

This and other objects and advantages of the invention will become obvious from the following detailed description.

THE INVENTION

The novel process of the invention for the preparation of a compound of the formula

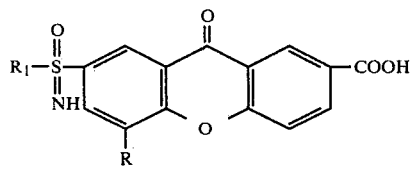

comprises reacting a phenol of the formula

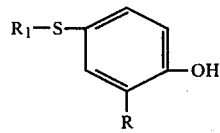

wherein R and $R_1$ have the above definitions with an acyl halide or anhydride of the formulae

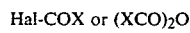

Hal-COX or (XCO)$_2$O wherein Hal is selected from the group consisting of chlorine and bromine and X is selected from the group consisting of alkyl of 1 to 3 carbon atoms and phenyl to obtain a compound of the formula

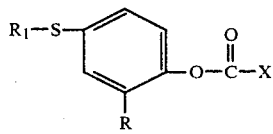

reacting the latter with a compound of the formula

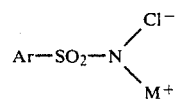

wherein Ar is an optionally substituted aryl and M is an alkali metal to obtain a compound of the formula

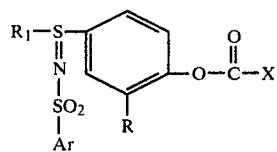

oxidizing the latter to obtain a compound of the formula

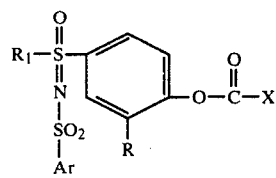

subjecting the latter to hydrolysis to obtain a compound of the formula

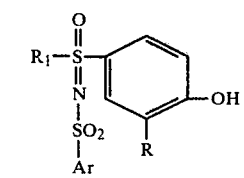

reacting the latter in the presence of a weak base and metallic copper or copper oxide with an isophthalate of the formula

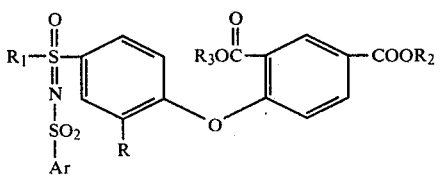

wherein $R_2$ and $R_3$ are individual ester groups and Hal is chlorine, bromine or iodine to obtain a compound of the formula

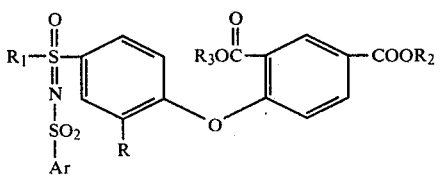

VIII and cyclizing the latter in the presence of a strong acid followed by hydrolysis to obtain the corresponding compound of formula I.

The process of the invention produces the compounds of formula I in good yields with a reduced number of steps and uses reactants more readily accessible than the prior art processes. Preferably, R is n-hexyl and $R_1$ is methyl.

In the compounds of formula IV, Ar is preferably a monocyclic aryl containing 6 to 10 atoms such as phenyl and is optionally substituted with at least one alkyl of 1 to 4 carbon atoms such as methyl. Ar is preferably p-tolyl and the reactant

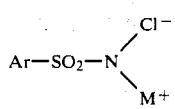

is preferably chloramine T in which Ar is p-tolyl.

In the compounds of formula VII, the esterifying groups $R_2$ and $R_3$ may be alkyl of 1 to 3 carbon atoms, aryl such as nitrophenyl, aralkyl such as nitrobenzyl and dialkylamino alkyl such as dimethylaminoethyl. The preferred $R_2$ and $R_3$ groups are selected so that the compounds of formula VIII are crystalline to facilitate purification.

In the preferred conditions of the process of the invention, the reaction of an acyl halide or anhydride with the phenol of formula II is effected in an anhydrous organic solvent such as pyridine and the reaction of the compound of formula III and the chloramine is effected in an anhydrous organic solvent, especially an alcohol such as isopropanol. The oxidation of the compound of formula IV is preferably effected with sodium periodate and ruthenium oxide in an anhydrous organic solvent such as dichloromethane. The reaction is effected in the presence of a peroxide and the periodates are normally used in an aqueous system or as in the present instance, in a two phase solvent system.

The hydrolysis of the product of formula V is preferably effected in an aqueous solution with a weak base such as sodium carbonate at the reflux temperature. The reaction of the compounds of formula VI and VII is effected in the presence of a weak base like sodium carbonate or potassium carbonate and metallic powdered copper at reflux. The cyclization is preferably effected at a temperature of 100° to 150° C. in the presence of a strong acid such as polyphosphoric acid or concentrated sulfuric acid. The hydrolysis may be effected simultaneously by the addition of water or in the case of an esterified compound, the hydrolysis may be effected in a separate step by known means.

In the following examples there are described several preferred embodiments to illustrate the invention. However, it is to be understood that the invention is not intended to be limited to the specific embodiments.

EXAMPLE 1

5-hexyl-7-(S-methyl-sulfonimidoyl)-xanthone-2-carboxylic acid

STEP A: 2-hexyl-4-methylthio-phenyl benzoate

A solution of 75 g of 2-hexyl-4-methylthio-phenol, 225 ml of pyridine and 100 g of benzoyl chloride was stirred at room temperature for 2 hours and then 450 ml of water were added thereto. The mixture was stirred for one hour and was filtered. The recovered product was washed with water and was dried to obtain 110 g of 2-hexyl-4-methylthio-phenyl benzoate melting at 57°–58° C.

STEP B: 2-hexyl-4-(S-methyl-N-tosyl-sulfimidoyl)-phenyl benzoate 50 g of the compound of Step A were added over 15 minutes at 50° C. to a solution of 43 g of chloramine T in 1000 ml of isopropanol and the mixture was stirred and filtered. The filtrate was cooled to 0° C. and crystallization occured. The mixture was vacuum filtered and the recovered product was dried to obtain 63 g of 2-hexyl-4-(S-methyl-N-tosyl-sulfimidoyl)-phenyl benzoate melting at 111°–112° C.

STEP C: 2-hexyl-4-(S-methyl-N-tosyl-sulfonimidoyl)-phenyl benzoate 100 mg of ruthenium oxide and 50 ml of an aqueous 10% sodium periodate solution were added to a solution of 50 g of the product of Step B in 250 ml of methylene chloride and the mixture was vigorously stirred to obtain a pale green emulsion which became a darker tint after a few minutes as periodate was consumed. The process was repeated 4 times using 50 ml of aqueous sodium periodate solution each time until a total of 25 g of sodium periodate was used. The separated aqueous phase was extracted with methylene chloride and the combined organic phases were washed with water, dried and evaporated to dryness to obtain raw 2-hexyl-4-(S-methyl-N-tosyl-sulfimidoyl)-phenyl benzoate in the form of an oil which was used as is for the next step. The oil could be crystallized to obtain the product melting at 90°–91° C.

STEP D: 2-hexyl-4-(S-methyl-N-tosyl-sulfonimidoyl)-phenol 500 ml of a 10% sodium carbonate solution was added to a solution of the oil of Step C in 250 ml of methanol and the mixture was stirred for 3 hours at 60° C. and was then cooled to room temperature. 100 ml of 20% hydrochloric acid were added to the mixture which was then extracted with chloroform. The organic phase was evaporated to dryness under reduced pressure and the residue was triturated with petroleum ether to obtain 40 g of 2-hexyl-4-(S-methyl-N-tosyl-sulfonimidoyl)-phenol melting at 109°–110° C.

STEP E: Dimethyl 4-[2-hexyl-4-(S-methyl-N-tosyl)-sulfonimidoyl)-phenoxy]-isophthalate A mixture of 20 g of the product of Step D, 15 g of dimethyl 4-bromo-isophthalate, 10 g of potassium carbonate, 1 g of powdered copper, 100 ml of nitrobenzene and 50 ml of toluene was slowly heated with stirring under an inert gas to 160° C. while distilling about 25 ml of toluene and the mixture was heated at 160° C. for 2 hours. The remaining solvent was then distilled and the residue was cooled and was dissolved in 400 ml of methylene chloride. The mixture was filtered and the filtrate was evaporated to dryness. The residue was dissolved in 250 ml of ether and the solution was cooled to 0° C. and was filtered. The recovered product was washed with ether and dried to obtain 15.7 g of dimethyl 4-[2-hexyl-4-(S-methyl-N-tosyl)-sulfonimidoyl)-phenoxy]-isophthalate melting at 124°–126° C. Concentration of the filtrate resulted in a second yield of 6.8 g of raw product.

STEP F: 5-hexyl-7-(S-methyl-sulfonimidoyl)-xanthone-2-carboxylic acid

A solution of 5 g of the product of Step E in 25 ml of concentrated sulfuric acid was heated at 120° C. for one hour and was then cooled. The mixture was poured with stirring into 250 ml of water and was filtered. The recovered product was washed with water and crystallized from methanol to obtain 2.5 g of 5-hexyl-7-(S-methyl-sulfonimidoyl)-xanthone-2-carboxylic acid melting at 193°–194° C.

EXAMPLE 2

5hexyl-7-(S-methyl-sulfonimidoyl)-xanthone-2-carboxylic acid

STEP A: 2-hexyl-4-methylthio-phenyl acetate

A solution of 6.6 g of 2-hexyl-4-methylthiophenol, 36 ml of pyridine and 18 ml of acetic anhydride was stirred overnight at room temperature and was then poured into water. The mixture was extracted with ether and the organic phase was washed with dilute aqueous hydrochloric acid, with aqueous sodium bicarbonate solution and then with water, dried and evaporated to dryness to obtain 7.45 g of 2-hexyl-4-methylthio-phenyl acetate.

STEP B: 2-hexyl-4-(S-methyl-N-tosyl-sulfimidoyl)-phenyl acetate

A mixture of 5 g of the product of Step A, 6.5 g of chloramine T trihydrate, 250 ml of dioxane and 125 ml of water was stirred for 5 hours and was then evaporated to dryness to obtain 11 g of an oil residue. The latter was chromatographed over silica gel and was eluted with chloroform to obtain 5 g of 2-hexyl-4-(S-methyl-N-tosyl-sulfimidoyl)-phenyl acetate which melted at 62°–65° C. after crystallization from petrolum ether.

STEP C: 2-hexyl-4-(S-methyl-N-tosyl-sulfonimidoyl)-phenyl acetate

A solution of 1 g of sodium periodate in water and 5 mg of ruthenium oxide were added to a solution of 1 g of the product of Step B in 40 ml of methylene chloride and after stirring the mixture for 30 minutes, another 5 mg of ruthenium oxide and 0.3 g of sodium periodate were added thereto. The mixture was stirred for 15 minutes and the separated organic phase was filtered. The filtrate was evaporated to dryness and the residue was chromatographed over silica gel. Elution with ethyl acetate yielded 0.88 g of 2-hexyl-4-(S-methyl-N-tosyl-sulfonimidoyl)-phenyl acetate in the form of an oil which solidified on cooling.

STEP D: 2-hexyl-4-(S-methyl-N-tosyl-sulfonimidoyl)-phenol

A suspension of 0.8 g of the product of Step C, 30 ml of a saturated sodium carbonate solution and 15 ml of ethanol was stirred at 50° C. for 15 minutes and the solution was cooled in water. The mixture was acidified with concentrated hydrochloric acid and was extracted with ether. The decanted organic phase was evaporated to dryness to obtain 0.65 g of 2-hexyl-4-(S-methyl-N-tosyl-sulfonimidoyl)-phenol which after crystallization from an ether-petroleum ether mixture melted at 107°–109° C.

STEP E: Dimethyl 4-[2-hexyl-4-(S-methyl-N-tosyl-sulfonimidoyl)-phenoxy]-isophthalate A solution of 0.4 g of the product of Step D, 0.3 g of dimethyl 4-bromoisophthalate and 10 ml of nitrobenzene was subjected to azeotropic distillation with benzene to remove all the water and then 50 mg of copper powder and 0.4 g of anhydrous potassium carbonate were added to the solution. The mixture was stirred at 160° C. under an inert atmosphere for 2 hours and was then cooled and diluted with chloroform. The mixture was filtered and the filtrate was evaporated to dryness under reduced pressure. The oily residue was triturated with petroleum ether to obtain 0.53 g of crystallized product. The latter was chromatographed over silica gel and was eluted with chloroform to obtain dimethyl 4-[2-hexyl-4-(S-methyl-N-tosyl-sulfonimidoyl)-phenoxy]-isophthalate in the form of white crystals melting at 115°–117° C.

STEP F: Methyl 5-hexyl-7-(S-methyl)-sulfonimidoyl)-Xanthone-2-carboxylate

A solution of 0.2 g of the product of Step E in 4 ml of polyphosphoric acid was stirred at 80° C. for 10 minutes and the temperature was then raised to 120° C. The mixture was stirred at 120° C. for 90 minutes and was then cooled and poured into water. The mixture was extracted with ethyl acetate and the organic phase was evaporated to dryness to obtain 0.11 g of a mixture of methyl 5-hexyl-7-(S-methyl)-sulfonimidoyl)-xanthone-2-carboxylate and the corresponding acid. The ester was obtained by chromatography over silica gel and elution with ethyl acetate.

STEP G: 5-hexyl-7-(S-methyl-sulfonimidoyl)-xanthone-2-carboxylic acid 2.7 ml of a 0.2 N aqueous sodium hydroxide solution were added to a solution of 0.1 g of the ester of Step F in 5 ml of ethanol and 1 ml of water and the mixture was refluxed for one hour and was cooled. The solution was acidified with 2 N hydrochloric acid and was then vacuum filtered. The recovered product was washed with water and dried to obtain 0.09 g of 5-hexyl-7-(S-methyl-sulfonimidoyl)-xanthone-2-carboxylic acid melting at 193°–194° C.

Various modifications of the process of the invention may be made without departing from the spirit or scope thereof and it should be understood that the invention is to be limited only as defined in the appended claims.

We claim:

1. A process for the preparation of a compound of the formula

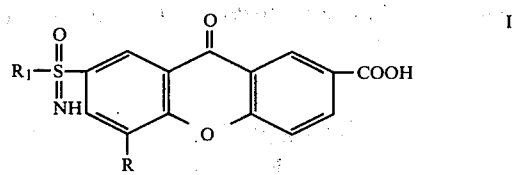

wherein R is selected from the group consisting of hydrogen and alkyl of 1 to 9 carbon atoms and $R_1$ is alkyl of 1 to 5 carbon atoms comprising reacting a phenol of the formula

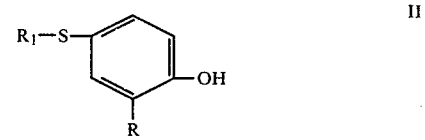

wherein R and $R_1$ have the above definitions with an acyl halide or anhydride of the formula

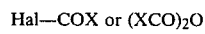

wherein Hal is selected from the group consisting of chlorine and bromine and X is selected from the group consisting of alkyl of 1 to 3 carbon atoms and phenyl to obtain a compound of the formula

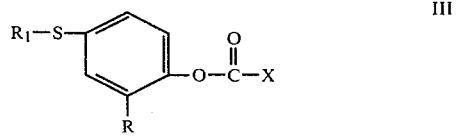

reacting the latter with a compound of the formula

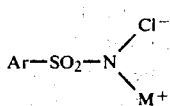

wherein Ar is an optionally substituted aryl and M is an alkali metal to obtain a compound of the formula

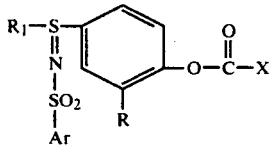

oxidizing the latter to obtain a compound of the formula

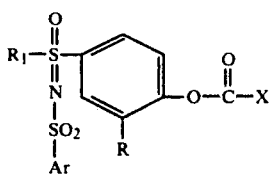

subjecting the latter to hydrolysis to obtain a compound of the formula

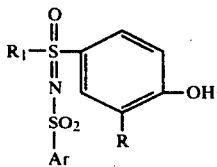

reacting the latter in the presence of a weak base and metallic copper or copper oxide with an isophthalate of the formula

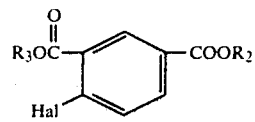

wherein $R_2$ and $R_3$ are individual ester groups and Hal is chlorine, bromine or iodine to obtain a compound of the formula

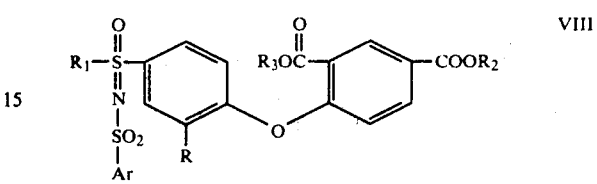

and cyclizing the latter in the presence of a strong acid followed by hydrolysis to obtain the corresponding compound of claim 1.

2. The process of claim 1 wherein R is n-hexyl and $R_1$ is methyl.

3. The process of claim 1 wherein Ar is p-tolyl.

4. The process of claim 1 wherein $R_2$ and $R_3$ are individually selected from the group consisting of alkyl of 1 to 3 carbon atoms, aryl, aralkyl and dialkylaminoalkyl of 1 to 3 alkyl carbon atoms.

5. The process of claim 1 wherein the phenol of formula II is reacted with an acyl halide or anhydride in an anhydrous organic solvent the reaction of the chloramine with the compound of formula III is effected in an anhydrous organic solvent, the oxidation of the compound of formula IV is effected with sodium meta periodate and ruthenium oxide in an anhydrous organic solvent, the hydrolysis of the compound of formula V is effected with an aqueous weak base at reflux, the reaction of the compounds of formulae VI and VII is effected in the presence of a weak base and powdered copper metal at reflux and the cyclization is effected at 100° to 150° C. in the presence of a strong acid.

* * * * *